US010421693B2

(12) United States Patent
Barr et al.

(10) Patent No.: US 10,421,693 B2
(45) Date of Patent: *Sep. 24, 2019

(54) COMPOSITION CONTAINING N-(N-BUTYL) THIOPHOSPHORIC TRIAMIDE ADDUCTS AND REACTION PRODUCTS

(71) Applicant: Koch Agronomic Services, LLC, Wichita, KS (US)

(72) Inventors: Douglas Barr, Decatur, GA (US); Ethel Garnier, Decatur, GA (US); Kwame Owusu-Adom, Grayson, GA (US)

(73) Assignee: Koch Agronomic Services, LLC, Wichita, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 15/644,217

(22) Filed: Jul. 7, 2017

(65) Prior Publication Data
US 2018/0022662 A1 Jan. 25, 2018
US 2019/0210936 A9 Jul. 11, 2019

Related U.S. Application Data

(63) Continuation of application No. 15/217,195, filed on Jul. 22, 2016, now Pat. No. 9,725,372.
(Continued)

(51) Int. Cl.
C05G 3/08 (2006.01)
C07F 9/22 (2006.01)
C05C 9/00 (2006.01)

(52) U.S. Cl.
CPC .............. C05G 3/08 (2013.01); C05C 9/00 (2013.01); C07F 9/224 (2013.01); Y02P 60/218 (2015.11)

(58) Field of Classification Search
CPC .......... C05G 3/08; C05G 3/0064; C05C 9/02; C05C 9/00; C09K 15/26; C09K 15/28
See application file for complete search history.

(56) References Cited

U.S. PATENT DOCUMENTS 9,725,372 B2 * 8/2017 Barr ..................... C05G 3/08
2007/0157689 A1 7/2007 Sutton et al.
(Continued)

FOREIGN PATENT DOCUMENTS

CN 101045656 A 10/2007
WO 2008002503 A2 1/2008
(Continued)

OTHER PUBLICATIONS

Official Action with Search Report dated Jun. 22, 2016 in corresponding Italian Application No. 102015000048766.
(Continued)

Primary Examiner — Jennifer A Smith

(57) ABSTRACT

Reaction products and methods for making and using such reaction products are provided. For example, a reaction product comprising an adduct formed from urea, formaldehyde, and a urease inhibitor is described, which can be provided in various forms. For example, such a reaction product can be in the form of a solid or solution. Such a reaction product can also be combined with one or more additional components, including but not limited to, additional urease inhibitor and/or a nitrogen-based fertilizer composition.

19 Claims, 2 Drawing Sheets

Related U.S. Application Data

(60) Provisional application No. 62/196,781, filed on Jul. 24, 2015.

(56) References Cited

U.S. PATENT DOCUMENTS

| | | | | |
|---|---|---|---|---|
| 2011/0296886 A1* | 12/2011 | Gabrielson | ............... | C05C 3/00 |
| | | | | 71/29 |
| 2013/0174623 A1* | 7/2013 | Gabrielson | ............. | C05C 9/005 |
| | | | | 71/29 |
| 2014/0047884 A1 | 2/2014 | Gabrielson et al. | | |
| 2017/0137335 A1* | 5/2017 | Barr | ........................ | C09K 15/26 |

FOREIGN PATENT DOCUMENTS

| | | |
|---|---|---|
| WO | 2011/137393 A1 | 11/2011 |
| WO | 2011137393 A1 | 11/2011 |
| WO | 2013123229 A1 | 8/2013 |
| WO | 2015/027244 A1 | 2/2015 |
| WO | 2015027244 A1 | 2/2015 |

OTHER PUBLICATIONS

International Search Report and Written Opinion received for PCT Patent Application No. PCT/US2016/043626, dated Oct. 31, 2016, 12 pages.

International Search Report and Written Opinion received for corresponding PCT Patent Application No. PCT/US2016/061620, dated Feb. 16, 2017, 10 pages.

International Preliminary Report on Patentability received for corresponding PCT Patent Application No. PCT/US2016/043626, dated Feb. 8, 2018, 7 pages.

Examination Report received Feb. 21, 2018 in corresponding Australian Application No. 2016297825, 3 pages.

Examination Report received Mar. 9, 2018 in corresponding Argentina Application No. P160102258, 9 pages (including translation).

Examination Report received Mar. 20, 2018 in corresponding New Zealand Application No. 739206, 4 pages.

Office Action received Mar. 26, 2018 in corresponding Chinese Application No. 201610591606.6, 8 pages (including translation).

International Search Report, for corresponding PCT application No. PCT/US2016/061620, dated May 24, 2018 (6 pages).

* cited by examiner

COMPOSITION CONTAINING N-(N-BUTYL) THIOPHOSPHORIC TRIAMIDE ADDUCTS AND REACTION PRODUCTS

CROSS REFERENCE TO RELATED APPLICATIONS

This application is a continuation of U.S. application Ser. No. 15/217,195 filed Jul. 22, 2016, which claims priority to U.S. Provisional Application No. 62/196,781 filed Jul. 24, 2015, both of which are herein incorporated by reference in their entirety.

FIELD OF THE DISCLOSURE

The present subject matter relates generally to compositions comprising urease inhibitors and to methods of preparing and using such compositions.

BACKGROUND

Fertilizers have been used for some time to provide nitrogen to the soil. The most widely used and agriculturally important nitrogen fertilizer is urea, $CO(NH_2)_2$. Most of the urea currently produced is used as a fertilizer in its granular (or prilled) form. After application of urea to soil, it is readily hydrolyzed to yield ammonia and carbon dioxide. This process is catalyzed by the enzyme urease, which is produced by some bacteria and fungi that may be present in the soil. The gaseous products formed by the hydrolysis reaction (i.e., ammonia and carbon dioxide) can volatilize to the atmosphere and thus, substantial losses from the total amount of the nitrogen applied to the soil can occur.

Attempts to reduce losses of applied nitrogen have utilized urease inhibitors and/or nitrification inhibitors as additives to the fertilizer. Urease inhibitors are compounds capable of inhibiting the catalytic activity of the urease enzyme on urea in the soil. Nitrification inhibitors are compounds capable of inhibiting the bacterial oxidation of ammonium to nitrate in the soil. Urease inhibitors and nitrification inhibitors can be associated with fertilizers in various ways. For example, they can be coated onto fertilizer granules or mixed into fertilizer matrices. A number of granulation methods are known, including falling curtain, spherudization-agglomeration drum granulation, prilling and fluid bed granulation technologies.

Examples of urease inhibitors are the thiophosphoric triamide compounds disclosed in U.S. Pat. No. 4,530,714 to Kolc et al., which is incorporated herein by reference. The disclosed thiophosphoric triamide compounds include N-(n-butyl) thiophosphoric triamide (NBPT), the most developed representative of this class of compounds. When incorporated into a urea-containing fertilizer, NBPT reduces the rate at which urea is hydrolyzed in the soil to ammonia. The benefits realized as a result of the delayed urea hydrolysis include the following: (1) nutrient nitrogen is available to the plant over a longer period of time; (2) excessive build-up of ammonia in the soil following the application of the urea-containing fertilizer is avoided; (3) the potential for nitrogen loss through ammonia volatilization is reduced; (4) the potential for damage by high levels of ammonia to seedlings and young plants is reduced; (5) plant uptake of nitrogen is increased; and (6) an increase in crop yields is attained. NBPT is commercially available for use in agriculture and is marketed in such products as the AGROTAIN® nitrogen stabilizer product line.

Industrial grade NBPT is a solid, waxy compound, and decomposes by the action of water, acid and/or elevated temperature. In particular, NBPT is believed to degrade at elevated temperatures into compounds that may not provide the desired inhibitory effects on the urease enzyme. Accordingly, its combination with other solid materials to provide a material capable of inhibiting urease, particularly via granulation with urea (which generally employs heat) can be challenging. As such, there is a need for urease inhibitor-containing compositions that can be combined with urea, desirably using current urea manufacturing practices, so as to produce fertilizer compositions that provide effective urease inhibition.

SUMMARY OF THE INVENTION

As disclosed herein, compositions comprising urease inhibitors are provided and methods for making such. Such compositions generally comprise a reaction product between a urease inhibitor (e.g., N-(n-butyl) thiophosphoric triamide, NBPT), urea, and formaldehyde. Such reaction products can be characterized as adducts, as the products arising from the reaction retain at least portions of two or more of the reactants (i.e., urease inhibitor, urea, and/or formaldehyde). Compositions arising from such reactions, comprising the disclosed reaction products, can be provided independently and can, in certain embodiments, be combined with other components. For example, such adduct-containing compositions can be combined with fertilizer materials comprising nitrogen sources, including but not limited to, urea, ammonia, ammonium nitrate, and combinations thereof. Advantageously, adduct-containing compositions disclosed herein, alone or in combination with one or more nitrogen sources, can provide fertilizers that exhibit substantial urease inhibitory effects and can thus be characterized by low ammonia volatilization losses in use (i.e., upon application to soil).

In one aspect, the present disclosure provides a composition comprising an adduct of NBPT, urea, and formaldehyde. In another aspect, the disclosure provides a composition comprising an adduct of NBPT, urea, and formaldehyde, and one or more materials selected from the group consisting of free NBPT, free formaldehyde, urea formaldehyde polymer (UFP), water, and combinations thereof. In a further aspect, the disclosure provides a composition comprising an adduct of NBPT, urea, and formaldehyde, wherein the composition comprises substantially no dicyandiamide. In a still further aspect, the disclosure provides a composition comprising one or more adducts of NBPT), urea, and formaldehyde, wherein the one or more adducts are represented by the following structures:

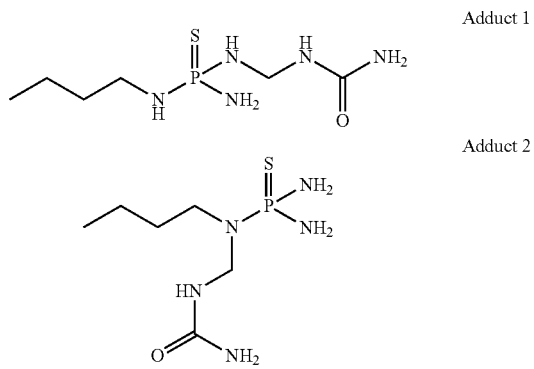

Adduct 3

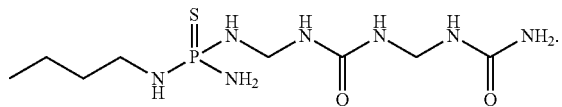

The compositions provided herein can, in some embodiments, be in the form of a solution of the adduct (e.g., with an organic solvent, such as those disclosed herein below). In certain embodiments, the composition is a synergistic mixture of free NBPT and the adduct. The disclosed compositions can, in some embodiments, comprise substantially no dicyandiamide (DCD). In some compositions, at least a portion (including all) of the urea and formaldehyde are in the form of a urea formaldehyde reaction product comprising dimethylolurea.

In another aspect, the present disclosure provides a fertilizer composition comprising urea and an adduct of NBPT, urea, and formaldehyde. Any of the compositions comprising an adduct of NBPT, urea, and formaldehyde as disclosed herein can be used in such fertilizer compositions. The fertilizer compositions can, in certain embodiments, comprise a significant amount of urea, e.g., at least about 90% by weight urea, at least about 95% by weight urea, at least about 98% by weight urea, at least about 99% by weight urea, or at least about 99.5% by weight urea.

In a further aspect, the present disclosure provides a method of forming a fertilizer composition, the method comprising combining a composition comprising an adduct of NBPT, urea, and formaldehyde as disclosed herein with a fertilizer material. The method can, in certain embodiments, comprise mixing the adduct-containing composition with solid particles of the fertilizer material and, in other embodiments, can comprise mixing the adduct-containing composition with a molten stream of the fertilizer material. In some embodiments, the method can further comprise combining free NBPT with one or both of the fertilizer material and the adduct-containing composition.

In another aspect, the disclosure provides a method of making a urease inhibiting fertilizer, the method comprising combining urea, formaldehyde, and NBPT such that an excess of urea is present, to form an adduct of NBPT, urea, and formaldehyde, which adduct remains incorporated into the remaining urea. In some embodiments, the urea and formaldehyde are in the form of a urea formaldehyde reaction product comprising dimethylolurea.

In a further aspect, the present disclosure provides a method of reducing hydrolysis of urea to ammonia in soil, comprising applying a composition comprising an adduct of NBPT, urea, and formaldehyde to the soil. Such methods can comprise combining a nitrogen source with the composition prior to said applying, applying the composition to the soil following application of a nitrogen source to the soil, or applying the composition to the soil prior to application of a nitrogen source to the soil.

In a still further aspect, the disclosure provides a method of incorporating an adduct of NBPT, urea, and formaldehyde into molten urea, comprising combining such an adduct (e.g., including, but not limited to, the adduct in the form of an adduct-containing composition) with molten urea. Additionally, the disclosure provides a method of forming an adduct of NBPT, urea, and formaldehyde, comprising contacting NBPT with a molten urea stream comprising formaldehyde and/or reaction products of urea and formaldehyde.

In one aspect, the disclosure specifically provides a composition comprising a mixture of: an adduct of N-(n-butyl) thiophosphoric triamide (NBPT), urea, and formaldehyde; and free NBPT. The disclosure further provides a fertilizer composition comprising urea and such a composition. It additionally provides a method of forming a fertilizer composition, the method comprising contacting a fertilizer material with such a composition and also a method of reducing hydrolysis of urea to ammonia in soil, comprising applying such a composition to the soil.

BRIEF DESCRIPTION OF THE DRAWINGS

In order to provide an understanding of embodiments of the invention, reference is made to the appended figures. These figures are exemplary only, and should not be construed as limiting the invention.

DETAILED DESCRIPTION OF THE INVENTION

Figure 1:
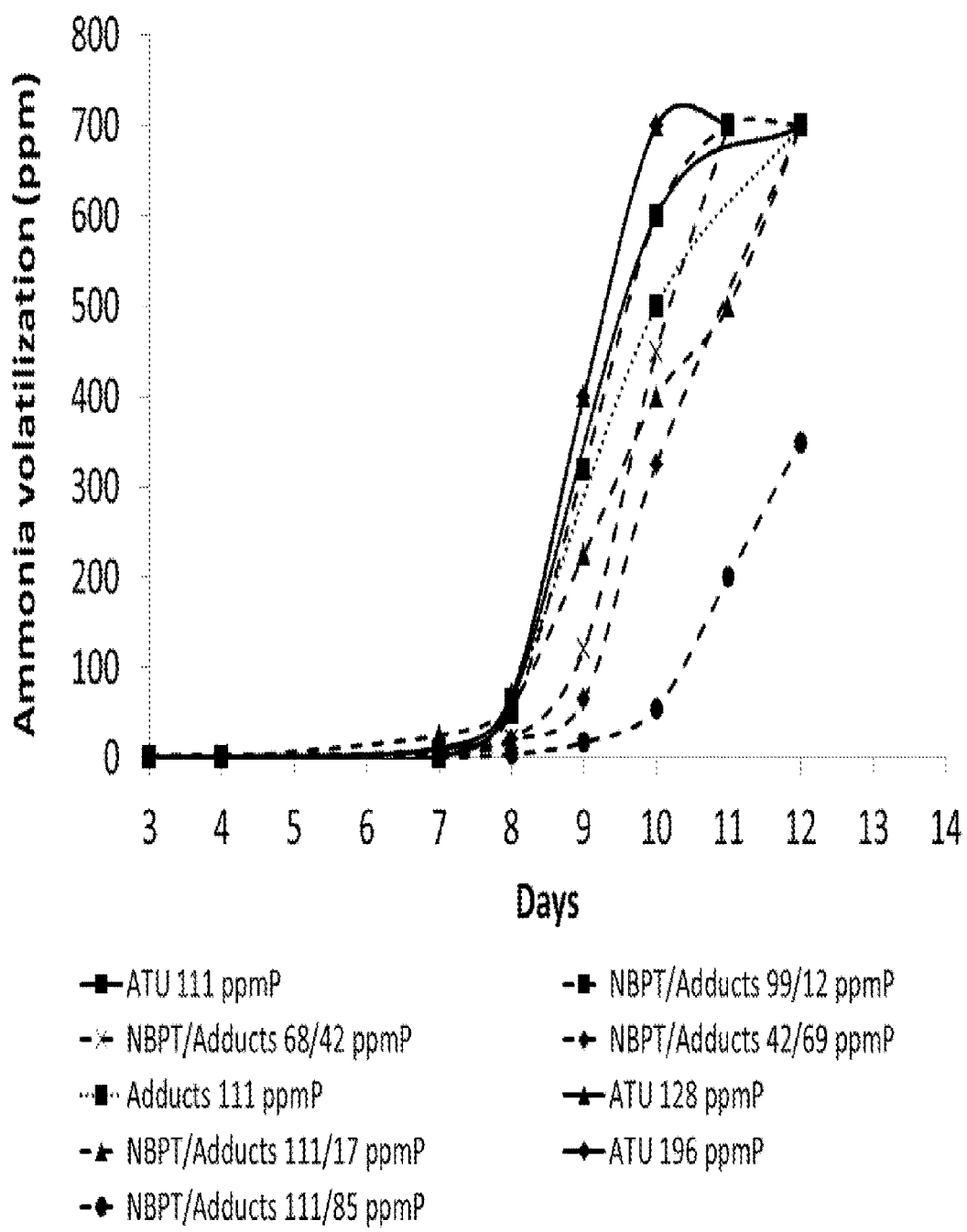
FIG. 1 is a plot of the effect of various urease inhibitors on ammonia volatilization (measured in ppm)

It is noted here that as used in this specification and the appended claims, the singular forms "a," "an," and "the" include plural reference unless the context clearly dictates otherwise. All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt. %" herein. All molecular weights as used herein are weight average molecular weights expressed as grams/mole, unless otherwise specified.

According to the present disclosure, compositions exhibiting effective urease inhibition and methods of producing such compositions are provided. It was surprisingly found that, as higher amounts of urease inhibitor were added to mixtures of urea and formaldehyde, the amount of free urease inhibitor present in the final product mixture did not scale accordingly. Subsequently, it was determined that at least a portion of the urease inhibitor added to the urea and formaldehyde was reacting under the conditions to which it was subjected to form an adduct comprising the urease inhibitor (thus decreasing the concentration of free urease inhibitor in the final product mixture). Such reaction products and compositions derived therefrom are described in further detail herein.

In particular, reaction products comprising adducts formed from one or more urease inhibitors with urea and/or formaldehyde are provided. Such reaction products can be provided as-formed, can be purified to isolate one or more components therefrom, or can be provided in combination with one or more other components, such as additional urease inhibitor or a fertilizer composition, e.g., in the form of a nitrogen source including, but not limited to, a urea source. The compositions disclosed herein can, in some embodiments, exhibit novel, slow-release of the one or more urease inhibitors.

As used herein, the term "urease inhibitor" refers to any compound that reduces, inhibits, or otherwise slows down the conversion of urea to ammonium ($NH_4^+$) in soil. Exemplary urease inhibitors include thiophosphoric triamides and phosphoric triamides of the general formula (I)

$$X=P(NH_2)_2NR^1R^2 \qquad (I)$$

where X=oxygen or sulfur, and $R^1$ and $R^2$ are independently selected from hydrogen, $C_1$-$C_{12}$ alkyl, $C_3$-$C_{12}$ cycloalkyl, $C_6$-$C_{14}$ aryl, $C_2$-$C_{12}$ alkenyl, $C_2$-$C_{12}$ alkynyl, $C_5$-$C_{14}$ heteroaryl, $C_1$-$C_{14}$ heteroalkyl, $C_2$-$C_{14}$ heteroalkenyl, $C_2$-$C_{14}$ heteroalkynyl, or $C_3$-$C_{12}$ cycloheteroalkyl groups.

In certain embodiments, urease inhibitors are N-(alkyl) thiophosphoric triamide urease inhibitors as described in U.S. Pat. No. 4,530,714 to Kolc et al., which is incorporated herein by reference. Particular illustrative urease inhibitors can include, but are not limited to, N-(n-butyl)thiophosphoric triamide, N-(n-butyl)phosphoric triamide, thiophosphoryl triamide, phenyl phosphorodiamidate, cyclohexyl phosphoric triamide, cyclohexyl thiophosphoric triamide, phosphoric triamide, hydroquinone, p-benzoquinone, hexamidocyclotriphosphazene, thiopyridines, thiopyrimidines, thiopyridine-N-oxides, N,N-dihalo-2-imidazolidinone, N-halo-2-oxazolidinone, derivatives thereof, or any combination thereof. Other examples of urease inhibitors include phenylphosphorodiamidate (PPD/PPDA), hydroquinone, N-(2-nitrophenyl) phosphoric acid triamide (2-NPT), ammonium thiosulphate (ATS) and organo-phosphorous analogs of urea, which are effective inhibitors of urease activity (see e.g. Kiss and Simihaian, Improving Efficiency of Urea Fertilizers by Inhibition of Soil Urease Activity. Kluwer Academic Publishers, Dordrecht, The Netherlands, 2002; Watson, Urease inhibitors. IFA International Workshop on Enhanced-Efficiency Fertilizers, Frankfurt. International Fertilizer Industry Association, Paris, France 2005).

In particular embodiments, the urease inhibitor can be or can include N-(n-butyl) thiophosphoric triamide (NBPT). The preparation of phosphoramide urease inhibitors such as NBPT can be accomplished, for example, by known methods starting from thiophosphoryl chloride, primary or secondary amines and ammonia, as described, for example, in U.S. Pat. No. 5,770,771, which is incorporated herein by reference. In a first step, thiophosphoryl chloride is reacted with one equivalent of a primary or secondary amine in the presence of a base, and the product is subsequently reacted with an excess of ammonia to give the end product. Other methods include those described in U.S. Pat. No. 8,075,659, which is incorporated herein by reference, where thiophosphoryl chloride is reacted with a primary and/or secondary amine and subsequently with ammonia. However this method can result in mixtures. Accordingly, when N-(n-butyl)thiophosphoric triamide (NBPT) or other urease inhibitors are used, it should be understood that this refers not only to the urease inhibitor in its pure form, but also to various commercial/industrial grades of the compound, which can contain up to 50 percent (or less), preferably not more than 20 percent, of impurities, depending on the method of synthesis and purification scheme(s), if any, employed in the production thereof. Combinations of urease inhibitors, for example using mixtures of NBPT and other alkyl-substituted thiophosphoric triamides, are known.

Representative grades of urease inhibitor may contain up to about 50 wt. %, about 40% about 30%, about 20% about 19 wt. %, about 18 wt. %, about 17 wt. %, about 16 wt. %, about 15 wt. %, about 14 wt. %, about 13 wt. %, about 12 wt. %, about 11 wt. %, 10 wt. %, about 9 wt. %, about 8 wt. %, about 7 wt. %, about 6 wt. %, about 5 wt. %, about 4 wt. %, about 3 wt. %, about 2 wt. %, or about 1 wt. % impurities, depending on the method of synthesis and purification scheme(s), if any, employed in the production of the urease inhibitor. A typical impurity in NBPT is $PO(NH_2)_3$ which can catalyze the decomposition of NBPT under aqueous conditions. Thus in some embodiments, the urease inhibitor used is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% pure.

For simplicity, the invention may be described in relation to embodiments wherein NBPT is the urease inhibitor. Description of the invention in terms wherein NBPT is the urease inhibitor should not be viewed as necessarily excluding the use of other urease inhibitors, or combinations of urease inhibitors, unless expressly noted.

The urea used to produce the adducts disclosed herein can be in various forms. For example, the urea can be a solid in the form of prills, flakes, granules, and the like, and/or a solution, such as an aqueous solution, and/or in the form of molten urea. At least a portion of the urea can be in the form of animal waste. Both urea and combined urea-formaldehyde products can be used according to the present disclosure. Illustrative urea-formaldehyde products can include, but are not limited to, urea-formaldehyde concentrate ("UFC") and urea-formaldehyde polymers ("UFP"). These types of products can be as discussed and described in U.S. Pat. Nos. 5,362,842 and 5,389,716 to Graves et al., for example, which are incorporated herein by reference. Any form of urea or urea in combination with formaldehyde can be used to make a UFP. Examples of solid UFP include PERGOPAK M® 2, available from Albemarle Corporation and NITAMIN 36S, available from Koch Agronomic Services, LLC. Any of these urea sources can be used alone or in any combination to prepare the reaction product disclosed herein.

As referenced hereinabove, in some embodiments, the formaldehyde used as a reagent to produce the reaction products disclosed herein can be provided in combination with the urea (e.g., in the form of a mixture or polymer with urea). In such embodiments, additional formaldehyde need not be added to form the desired adduct, although the disclosure is not limited thereto and it is possible to add additional formaldehyde to such urea-formaldehyde products.

In some embodiments, formaldehyde is intentionally added as a reagent to prepare the reaction products disclosed herein, and the formaldehyde can be in various forms. For example, paraform (solid, polymerized formaldehyde) and/or formalin solutions (aqueous solutions of formaldehyde, sometimes with methanol, in about 10 wt. %, about 20 wt. %, about 37 wt. %, about 40 wt. %, or about 50 wt. %, based on the weight of the formalin solution) are commonly used forms of formaldehyde. In some embodiments, the formaldehyde can be an aqueous solution having a concentration of formaldehyde ranging from about 10 wt. % to about 50 wt. % based on total weight of the aqueous solution. Formaldehyde gas can also be used. Formaldehyde substituted in part or in whole with substituted aldehydes such as acetaldehyde and/or propylaldehyde can also be used as the source of formaldehyde. Any of these forms of formaldehyde sources can be used alone or in any combination to prepare the reaction product described herein.

The method of preparing the reaction product disclosed herein can vary. Generally, NBPT is combined with, mixed, or otherwise contacted with urea and formaldehyde. Accordingly, in some embodiments, the disclosure provides a method for making an adduct, comprising combining urea, formaldehyde, and NBPT such that at least one adduct is formed. For example, at least a portion of the NBPT can react with at least a portion of the urea and/or at least a portion of the formaldehyde to form one or more structurally different adducts, as will be described further hereinafter.

The reactants (i.e., urea, formaldehyde, and NBPT) can be combined with one another in any order or sequence. For example, in one embodiment, urea and formaldehyde are first combined and NBPT is added thereto. In another embodiment, urea and a urea formaldehyde product (e.g., urea formaldehyde concentrate or urea-formaldehyde polymer) are combined and NBPT is added thereto. In a further embodiment, a urea formaldehyde product and formaldehyde are combined and NBPT is added thereto. In a still further embodiment, urea and NBPT are combined and formaldehyde or a urea formaldehyde product is added thereto. Additionally, in certain embodiments, other components can be included at any of these stages, alone, or in combination with the urea, formaldehyde, or NBPT. For example, in some embodiments, a nitrification inhibitor (such as those disclosed herein below) can be combined with one or more of the components, e.g., including but not limited to, embodiments wherein the nitrification inhibitor is combined with NBPT and this mixture is combined with the other components.

In these various embodiments, the form of the NBPT added can vary. For example, the NBPT can be used in molten liquid form, in solution form, or in suspension/dispersion form. Similarly, the form of the material with which the NBPT is combined (i.e., the urea/formaldehyde mixture, the urea/urea formaldehyde product mixture, or the urea formaldehyde product/formaldehyde mixture) can vary. For example, in some embodiments, the material with which the NBPT is combined can be in solution form, can be in dispersion/suspension form, or can be in the form of a molten urea liquid. In either case, the form of the NBPT, urea, and formaldehyde should allow for a high degree of contact between the reagents to facilitate the reaction and formation of adducts. The most preferred form of NBPT is a solution or suspension/dispersion. The most preferred form of urea/formaldehyde mixture, urea/urea formaldehyde product mixture, urea formaldehyde product/formaldehyde mixture is solution or molten urea liquid containing the formaldehyde. In another embodiment that employs a MAP, DAP, or AMS catalyst to facilitate the reaction, the form of urea/formaldehyde mixture, urea/urea formaldehyde product mixture, urea formaldehyde product/formaldehyde mixture can be a solid (i.e. urea granule) and form of NBPT a solution Where solvents are used at any stage of the combining process, the solvents employed are generally those sufficient to solubilize one or more of the NBPT, urea, and/or formaldehyde. Suitable solvents can include, for example, water (including aqueous buffers), N-alkyl 2-pyrrolidones (e.g., N-methyl pyrrolidone), glycols and glycol derivatives, ethyl acetate, propylene glycol, benzyl alcohol, and combinations thereof. Representative solvents known to solubilize NBPT include, but are not limited to, those solvents described in U.S. Pat. Nos. 5,352,265 and 5,364,438 to Weston, U.S. Pat. No. 5,698,003 to Omilinsky et al., U.S. Pat. Nos. 8,048,189 and 8,888,886 to Whitehurst et al., WO2014/100561 to Ortiz-Suarez et al., WO2014/055132 to McNight et al., WO2014/028775 and WO2014/028767 to Gabrielson et al., and EP2032589 to Cigler, which are incorporated herein by reference. In certain embodiments, the solvent, or mixture of solvents, employed to combine the components can be selected from the group consisting of water (including buffered solutions, e.g., phosphate buffered solutions), glycols (e.g., propylene glycol), glycol derivatives and protected glycols (e.g., glycerol including protected glycerols such as isopropylidine glycerol, glycol ethers e.g. monoalkyl glycol ethers, dialkyl glycol ethers), acetonitrile, DMSO, alkanolamines (e.g., triethanolamine, diethanolamine, monoethanolamine, alkyldiethanolamines, dialkylmonoethanolamines, wherein the alkyl group can consist of methyl, ethyl, propyl, or any branched or unbranched alkyl chain), alkylsulfones (e.g., sulfolane), alkyl amides (e.g., N-methylpyrrolidone, N-ethylpyrrolidone, dimethylformamide, or any non-cyclic amide), monoalcohols (e.g., methanol, ethanol, propanol, isopropanol, benzyl alcohol), dibasic esters and derivatives thereof, alkylene carbonates (e.g., ethylene carbonate, propylene carbonate), monobasic esters (e.g., ethyl lactate, ethyl acetate), carboxylic acids (e.g., maleic acid, oleic acid, itaconic acid, acrylic acid, methacrylic acid), glycol esters, and/or surfactants (e.g. alkylbenzenesulfonates, lignin sulfonates, alkylphenol ethoxylates, polyalkoxylated amines) and combinations thereof. Further co-solvents, including but not limited to, liquid amides, 2-pyrrolidone, N-alkyl 2-pyrrolidones, and non-ionic surfactants (e.g., alkylaryl polyether alcohols) can be used in certain embodiments.

Various other additives that do not negatively impact the formation of the adducts disclosed herein can be included in the reaction mixture (i.e., urease, inhibitor(s), urea, formaldehyde, and optional solvent(s)). For example, components (e.g., impurities) that are generally present in urea and/or formaldehyde are commonly incorporated in the reaction mixture. In some embodiments, components that are desirably included in the final product can be incorporated into the reaction mixture (e.g., dyes, as described in further detail below).

In certain embodiments, monoammonium phosphate (MAP), diammonium phosphate (DAP), and/or ammonium sulfate (AMS) can be used to promote the formation of adducts. Although not intended to be limiting, it is believed that MAP, DAP, or AMS can function as catalysts to facilitate the formation of the adducts disclosed herein. In some embodiments, it may be possible, by including MAP, DAP, and/or AMS (and/or other catalysts), to reduce the reaction time and/or to conduct the reaction at lower temperatures than would otherwise be required to form the adducts. In certain embodiments, mixing granules of NBPT-treated urea with granules of MAP, DAP or AMS also accelerates formation of the adducts disclosed herein as compared with embodiments wherein no catalyst is employed. In some embodiments, the use of a particular catalyst may have an effect on the amount and/or type(s) of various adducts formed during the reaction.

Adduct formation can be conducted at various pH values, and in some embodiments, it may be desirable to adjust the pH of the reaction mixture (e.g., by adding acid and/or base). Representative acids include, but are not limited to, solutions of mineral acids such as hydrochloric acid, sulfuric acid, nitric acid, phosphoric acid, and combinations thereof. Exemplary bases include, but are not limited to, solutions of ammonia, amines (e.g., primary, secondary and tertiary amines and polyamines), sodium hydroxide, potassium hydroxide, and combinations thereof. In some embodiments, it may be desirable to employ a buffer solution to control the pH of the reaction mixture. Representative buffer solutions include, but are not limited to, solutions of triethanolamine, sodium borate, potassium bicarbonate, sodium carbonate, and combinations thereof.

The conditions under which the NBPT, urea, and formaldehyde (and optionally, other additives) are combined can vary. For example, the reaction can be conducted at various temperatures, e.g., ranging from ambient temperature (about 25° C.) to elevated temperatures (above 25° C.). In certain embodiments, the temperature at which the reaction is conducted is at least about 50° C., at least about 60° C., at least about 70° C., at least about 80° C., at least about 90° C., or at least about 100° C., such as about 20° C. to about 150° C.

Advantageously, in some embodiments, the reaction product can be prepared under conditions of conventional urea manufacturing (as described, for example, in Jozeef Meesen, Ullman's Encyclopedia of Industrial Chemistry (2012), vol. 37, pages 657-695, which is incorporated herein by reference). Such urea manufacturing conditions generally include temperatures at which urea is in molten form, e.g., temperatures of about 130° C. to about 135° C. For example, in such embodiments, the NBPT can be added to a molten mixture of urea and formaldehyde (or urea and urea-formaldehyde (i.e., UF, UFC or UFP)). The mixture can be combined and then cooled to provide a reaction product comprising the reaction product, i.e., adduct of NBPT, urea, and formaldehyde. For example, the composition can be cooled by subjecting the reaction mixture to typical urea pastillation, prilling or granulation processes (e.g., fluidized bed granulation, drum granulation, sprouted bed granulation, and the like), which generally comprise a cooling step following formation of pastilles, prills and/or granules. Generally, the drying process provides the reaction product in the form of a solid material (e.g., a pastillated, granular or prilled solid).

The NBPT, urea, and formaldehyde (i.e., the reaction mixture) can be maintained together under the reaction conditions for various periods of time. For example, in some embodiments, the reaction can be conducted within a relatively short period (e.g., on the order of minutes, e.g., about 30 seconds to about 30 minutes, about 1 to about 20 minutes, or about 1 to about 10 minutes. In some embodiments, the reaction may be conducted for about 1 minute or longer, about 2 minutes or longer, about 5 minutes or longer, about 10 minutes or longer, about 15 minutes or longer, or about 20 minutes or longer. In certain embodiments, the reaction can be conducted for about 2 hours or less, about 1 hour or less, about 30 minutes or less, about 25 minutes or less, about 20 minutes or less, about 15 minutes or less, or about 10 minutes or less. In some embodiments, the components can be reacted together for a somewhat longer period, e.g., for a period of about 2 hours or longer, about 4 hours or longer, about 6 hours or longer, about 8 hours or longer, about 10 hours or longer, about 12 hours or longer, about 14 hours or longer, about 16 hours or longer, about 18 hours or longer, about 20 hours or longer, about 22 hours or longer, or about 24 hours or longer. In some embodiments, the reaction time is about 2 hours to about 48 hours, such as about 4 hours to about 36 hours.

In certain embodiments, the amount of time for which the reaction conducted may be that amount of time required to convert a given percentage of NBPT in the reaction mixture to adduct form. For example, in one embodiment, the reaction mixture is reacted to about 10% or less free (i.e., unreacted) NBPT by weight, based on total NBPT added to the reaction mixture or to about 5% or less free NBPT by weight, based on total NBPT added to the reaction mixture. In another embodiment, the reaction mixture is reacted to about 40% or less free (i.e. uneacted) NBPT by weight, based on the total NBPT added to the reaction mixture, or to about 30% or less free NBPT by weight, based on total NBPT added to the reaction mixture, or to about 20% or less free NBPT by weight, based on total NBPT added to the reaction mixture. In yet another embodiment, the reaction mixture is reacted to about 2% or less free NBPT by weight, based on total NBPT added to the reaction mixture, or to about 1% or less free NBPT by weight, based on total NBPT added to the reaction mixture, or to about 0.1% or less free NBPT by weight, based on total NBPT added to the reaction mixture. In a further embodiment, the reaction mixture is reacted to about 50% (i.e. unreacted) NBPT by weight, based on the total NBPT added to the reaction mixture to create a 1:1 wt. % adduct:free NBPT product (as measured by phosphorous content). In yet a further embodiment, the reaction mixture is reacted to create a weight ratio of adduct:free NBPT product in the range from about 4:1 to 1:4 (as measured by phosphorous content), including 3:1 to 1:3, 2:1 to 1:2, and a 1:1. Accordingly, in some embodiments, the method of producing an adduct as described herein further comprises monitoring the amount of free NBPT remaining over the course of the reaction and evaluating the completeness of reaction based on the amount of free NBPT in comparison to the desired maximum content of free NBPT by weight to be included in the reaction product.

It is noted that the particular reaction components may affect the reaction conditions required to produce the reaction product. For example, reaction of components in one solvent may be more efficient than reaction of those components in a different solvent and it is understood that, accordingly, less time and/or lower temperature may be required for adduct formation in the former case. Also, where a catalyst is employed, less time and/or lower temperature may be required for adduct formation. It is also noted that, in some embodiments, employing different reaction conditions can have an effect on the amount and/or type(s) of various adducts formed during the reaction.

The reaction products provided according to the methods disclosed hereinabove can comprise one or a plurality of structurally different adducts. For example, a given reaction product can comprise at least one adduct, at least two different adducts, at least three different adducts, at least four different adducts, at least five different adducts, at least ten different adducts, at least twenty-five different adducts, at least about fifty different adducts, or at least about one hundred different adducts. The adducts may be in the form of discrete compounds, oligomers, polymers, and combinations thereof. The overall amount of adduct formed can vary and, likewise, the amount of each different adduct (where more than one adduct is present in the composition) can vary.

Certain representative adducts that have been identified in reaction products, based on reactions between urea, formaldehyde, and NBPT, are as follows (wherein the reference to these adducts as "Adduct 1," "Adduct 2," and "Adduct 3" are arbitrary names chosen to distinguish them from one another and from other adducts that may be present in various reaction products):

Adduct 1

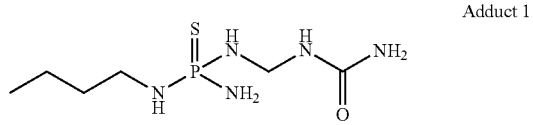

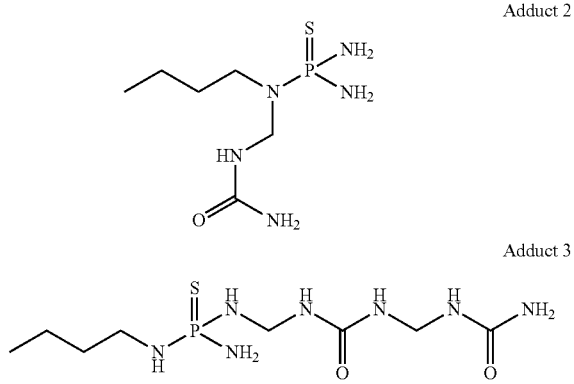

Adduct 2

Adduct 3

The reaction product can comprise various other components in addition to the adduct(s). It is to be understood that other components that may be present in the reaction product can be a result of the specific method used to produce the reaction product and, particularly, of the amount of each reactant included in the reaction mixture. For example, where the reaction conditions are such that there is an excess of one or two reactants, the reaction product may comprise free reactant (i.e., reactant which is not incorporated into an adduct). In various embodiments, the reaction product can comprise at least some percent by weight of one or more components selected from the group consisting of free NBPT, free formaldehyde, free urea, free urea-formaldehyde products (e.g., UFP), catalyst (e.g., MAP, DAP, or MAS), impurities (e.g., arising from the grade of reactants used), solvent, water, and combinations thereof. The relative amounts of such components can vary, with exemplary amounts and ratios disclosed below.

The reaction products disclosed herein can include widely varying mole percentages of urea, formaldehyde, and NBPT (including complexed and free forms of each component, e.g., as determined by elemental analysis). Similarly, the reaction products disclosed herein can have widely varying molar ratios, particularly as the method of producing the adduct-containing compositions can vary. In some specific embodiments, the reaction products can have a molar ratio of about 1:0.5 to about 1:2 NBPT:urea (including complexed and free forms of each component, e.g., as determined by elemental analysis). In certain embodiments, urea is used in great excess with respect to the NBPT; consequently, in such embodiments, the molar ratio of NBPT:urea is significantly lower. In some specific embodiments, the reaction products can have a molar ratio of about 1:0.5 to about 1:2 NBPT:formaldehyde (including complexed and free forms of each component, e.g., as determined by elemental analysis). Again, in some embodiments, the formaldehyde is present in significant excess with respect to the NBPT and, in such embodiments, the molar ratio of NBPT:formaldehyde is significantly lower.

The reaction products disclosed herein can advantageously exhibit effective urease inhibition and, in preferred embodiments, can exhibit slow release of NBPT, providing extended urease inhibition properties. Accordingly, the urease inhibition exhibited by these reaction products can be achieved over a longer period of time than that exhibited by a comparable composition comprising only free (i.e., unreacted) NBPT. Surprisingly, the reaction products, in some embodiments, can exhibit effective urease inhibition even at NBPT levels that have been established as ineffective. In other words, a reaction product prepared using a given amount of NBPT can, in some embodiments, exhibit effective urease inhibition even where a comparable composition comprising that same amount of NBPT in free (i.e., unreacted) form does not show significant urease inhibition.

The reaction product obtained according to the methods disclosed herein can be used or stored for later use in the form in which it is provided, can be treated in some manner before being used or stored for later use (e.g., to provide it in a different form or to isolate one or more components therefrom), and/or can be combined with other components before being used or stored for later use. Various compositions comprising at least a portion of the reaction products disclosed herein are disclosed herein below.

For example, in one embodiment, the reaction product is maintained substantially in the form in which it is provided following reaction (e.g., in undiluted liquid or solid form, in solution form, in suspension/dispersion form, in the form of urea-based granules comprising the adduct, and the like). As noted above, such forms can, in some embodiments, comprise other components, e.g., residual reactants and/or solvent. The specific form of these as-formed reaction products may, in certain embodiments, be further modified prior to use and/or storage, e.g., by concentrating solution or suspension/dispersion forms by removing solvent therefrom, by diluting any of the forms by adding one or more solvents thereto, by solubilizing solid forms, or by contacting a solid, undiluted liquid, solution, or suspension/dispersion form with a solid support so as to provide the reaction product in solid form. In one particular embodiment, the reaction product is provided in homogenous solution form.

In another embodiment, the reaction product is treated so as to isolate one or more adducts therefrom. For example, the reaction product can be treated so as to remove any or all components other than the adducts from the reaction product to obtain a mixture comprising all adducts, a mixture comprising some adducts, or one or more single, isolated adducts. Such isolated mixtures or single adducts can be provided in their natural forms (e.g., in solid or liquid, substantially pure form) or can be treated as described with regard to the as-formed reaction products modified prior to use or storage (e.g., to provide a solution or suspension/dispersion of the adduct or adducts by adding one or more solvents thereto, or to provide an adduct or adduct mixture in solid form by contacting the adduct or adduct mixture in solid, undiluted liquid, solution, or suspension/dispersion form with a solid support).

In a further embodiment, the reaction product (as-formed, or modified as noted above) or the isolated adduct(s) (as-provided, or modified as noted above) can be combined with one or more other components. For example, certain compositions are provided which comprise the reaction product admixed with one or more other components, e.g., one or more nitrogen sources (e.g., urea or a urea formaldehyde product) or free NBPT. Certain compositions are provided which comprise the one or more isolated adducts admixed with one or more other components, e.g., one or more nitrogen sources (e.g., urea or a urea formaldehyde product) or free NBPT. Again, any of these combinations can be in varying forms (e.g., in solid form, undiluted liquid form, solution form, dispersion/suspension form, and the like).

As-Formed Reaction Product

As described in detail above, the reaction products provided herein can comprise varying amounts of adduct(s) and can further comprise varying amounts of other components.

The particular makeup of the reaction product can determine the methods of use for which that reaction product is particularly suited.

For example, where a reaction product is provided that comprises a significant free urea content and/or a significant urea-formaldehyde product content, the reaction product (in varying physical forms, e.g., as described above) can be employed as a fertilizer composition. For example, although not intending to be limited, reaction products comprising at least about 90% urea, at least about 95% urea, at least about 98% urea, or at least about 99% urea can be used as fertilizer compositions. As the reaction products can contain varying amounts of urea and/or urea-formaldehyde product, the amount of the reaction product to be applied as a fertilizer composition can vary accordingly. The rate at which such compositions are applied to soil may, in some embodiments, be identical to the rate at which urea is currently used for a given application or can be scaled accordingly (e.g., based on the weight percent of urea contained within the reaction product).

A reaction product comprising a high concentration of urea can broadly be used in all agricultural applications in which urea is currently used. These applications include a very wide range of crop and turf species, tillage systems, and fertilizer placement methods. The compositions disclosed herein are useful for fertilizing a wide variety of seeds and plants, including seeds used to grow crops for human consumption, for silage, or for other agricultural uses. Indeed, virtually any seed or plant can be treated in accordance with the present invention using the compositions of the present invention, such as cereals, vegetables, ornamentals, conifers, coffee, turf grasses, forages and fruits, including citrus. Plants that can be treated include grains such as barley, oats and corn, sunflower, sugar beets, rape, safflower, flax, canary grass, tomatoes, cotton seed, peanuts, soybean, wheat, rice, alfalfa, sorghum, bean, sugar cane, broccoli, cabbage and carrot. Application of a reaction product containing a significant urea concentration to soil and/or plants can increase the nitrogen uptake by plants, enhance crop yields, and minimize the loss of nitrogen from the soil.

Such reaction products can be useful in fertilizing and inhibiting urease in various types of soils. Although not limited thereto, such compositions in certain embodiments, find particular use in very acidic soil. It is generally understood that acidic soil degrades NBPT; however, the presently disclosed reaction products have been shown to perform well in acidic soil (e.g., better than urea-based fertilizer combined with an equivalent amount of free NBPT).

In some embodiments, the reaction product is used (in varying forms, e.g., as described above, including in isolated adduct form) in combination with one or more fertilizer compositions. Such methods are applicable both for reaction products comprising a significant urea concentration and reaction products comprising a lower urea concentration (including reaction products comprising little to no free urea). For example, the reaction product can be applied to the soil before, concurrently with, or after application of a nitrogen-based fertilizer composition. The reaction product can be combined with the fertilizer composition, e.g., within the soil, on or about the surface of the soil, or a combination thereof. The urea can include any of the types of urea disclosed hereinabove, such as free urea, urea-formaldehyde products, and the like and additionally can include various substituted ureas. Another suitable urea source can be or can include animal waste(s) such as urine and/or manure produced by one or more animals, e.g., cows, sheep, chickens, buffalo, turkeys, goats, pigs, horses, and the like.

In some embodiments, the urea source can be or can include animal waste such as urine and/or manure deposited on and/or in the soil or the nitrogen source can be or can include a fertilizer product previously applied to the soil. As such, the reaction product can be applied to the soil and mixed with the animal waste and/or previously applied fertilizer(s) on the surface of and/or within the soil. The reaction product can be applied to the soil before, during, and/or after the animal waste and/or fertilizer(s) are deposited on/in the soil. In another example, the urea source can be or can include animal waste such as urine and/or manure that can be collected and placed within a holding tank, pond, or the like, and the reaction product can be added to the animal waste to provide a mixture. The resulting mixture can then be deposited about the soil to act as a fertilizer therein.

Reaction Product+Free NBPT

In certain embodiments, the reaction product (in varying forms, e.g., as described above, including in isolated adduct form) can be combined with additional free urease inhibitor (e.g., including, but not limited to, additional free NBPT). The reaction product and free urease inhibitor can, in some embodiments, be combined during use (e.g., the reaction product can be applied to the soil before, concurrently with, or after application of free NBPT).

In certain embodiments, the reaction product and free urease inhibitor can be provided within a single composition. The free urease inhibitor combined with the reaction product can be the same urease inhibitor or a different urease inhibitor than that present in the adduct or can be a combination of the same urease inhibitor and a different urease inhibitor. In such compositions, the free urease inhibitor (e.g., NBPT) can be present in varying amounts. The adduct and free urease inhibitor can be provided in roughly equivalent amounts, the amount of NBPT may be greater than the amount of adduct, or the amount of NBPT may be less than the amount of adduct. In some embodiments, the molar ratio of NBPT:adduct is between about 1:1 and about 1:10, e.g., between about 1:1 and about 1:7. In other embodiments, the molar ratio may be between about 10:1 and about 1:1, e.g., between about 7:1 and about 1:1. In other embodiments, the weight ratio of adduct to free NBPT product is in the range from about 4:1 to 1:4 (as measured by phosphorous content), including 3:1 to 1:3, 2:1 to 1:2, and a 1:1. Such embodiments can include a solution of adduct and free NBPT, or a fertilizer (solid or molten) comprising adduct and free NBPT. A solution of adduct and free NBPT may contain between about 15 wt. % in total of adduct and free NBPT to about 50 wt. % in total of adduct and free NBPT, including about 20 wt. % in total of adduct and free NBPT to about 40 wt. % in total of adduct and free NBPT, and about 25 wt. % in total of adduct and free NBPT to about 30 wt. % in total of adduct and free NBPT.

As noted above, the reaction product disclosed herein may, in some embodiments, already contain some percentage of free (unreacted) NBPT, which was added to the reaction mixture (but which did not react under the reaction conditions to form an adduct). Accordingly, in some embodiments, free NBPT can be added to the reaction product to bring the total amount of free NBPT to within the desired range. In other embodiments (e.g., wherein the reaction product is in the form of isolated adduct form), little to no NBPT is understood to be present in the isolated single adducts or mixtures thereof; accordingly, sufficient free NBPT must be added to bring the free NBPT content of the resulting composition within the ranges referenced above.

Surprisingly, the adducts disclosed herein in combination with free NBPT can, in some embodiments, exhibit synergistic activity. For example, when a reaction product is combined with free NBPT, the resulting composition can exhibit greater urease inhibition than would be expected based on the urease inhibition of a comparable amount of NBPT, all in free (unreacted) form, or than would be expected based on the urease inhibition of a comparable amount of adducts alone.

In certain embodiments, the reaction product/free NBPT compositions can be directly employed as fertilizer compositions (i.e., where the reaction product comprises a significant free urea content and/or a significant urea-formaldehyde product content). However, more commonly, such reaction product/free NBPT compositions are used in combination with a nitrogen source. In such embodiments, a composition comprising the reaction product and free NBPT can be applied in varying forms (e.g., in liquid, solution, dispersion/suspension, or solid form) to the soil before, concurrently with, or after application of a nitrogen-based fertilizer composition. The nitrogen-based fertilizer can include, for example, any of the types of urea and urea-formaldehyde products disclosed hereinabove. The composition can be combined with the fertilizer composition, e.g., within the soil, on or about the surface of the soil, or a combination thereof. The reaction product/free NBPT composition advantageously provides effective urease inhibition with regard to the nitrogen-based fertilizer composition.

Reaction Product+Urea

The reaction product can, in some embodiments, be combined with a nitrogen source to provide an adduct-containing fertilizer composition. For example, the reaction product (in various forms, including isolated adduct form) can, in some embodiments, be combined (e.g., mixed, blended, or otherwise combined) with one or more nitrogen sources (e.g., urea or urea-formaldehyde products). The relative amounts of adduct and urea in such a fertilizer composition can vary, and in certain embodiments, the amount of adduct can be, for example, within the range of about 1ppm to about 10,000 ppm adduct in the fertilizer composition, including about 20 ppm to about 1000 ppm, and about 100 ppm to about 800 ppm. Additionally, the amount of adduct in the fertilizer can be measured on a phosphorous basis (i.e. ppmP from the adducts), and includes the ranges of about 20 ppmP to about 1000 ppmP, 50 ppmP to about 500 ppmP, and 20 ppmP to 250 ppmP. A composition provided by combining the reaction product with urea can provide a fertilizer composition comprising up to about 95% by weight urea, up to about 98% by weight urea, up to about 99% by weight urea, up to about 99.5% by weight urea or up to about 99.9% by weight urea, e.g., between about 95% and about 99.9% by weight urea, between about 98% and about 99.9% by weight urea, or between about 99% and about 99.9% by weight urea, and the like.

In certain embodiments, the reaction product can be blended directly with granulated urea or can be used as an additive to liquid (molten) urea. The combining of reaction product with urea can be done at ambient temperature or at elevated temperature, e.g., at least about 50° C., at least about 60° C., at least about 70° C., at least about 80° C., at least about 90° C., or at least about 100° C., such as about 20° C. to about 150° C. Advantageously, in some embodiments, the reaction product can be combined with urea under conditions of conventional urea manufacturing generally including temperatures at which urea is in molten form, e.g., temperatures of about 130° C. to about 135° C. In such embodiments, it is beneficial to ensure that sufficient mixing is employed during this combining step so that the adduct is substantially homogeneously distributed within the molten urea, particularly before the urea melt cools and solidifies in the subsequent granulation step.

The reaction product can be combined with the urea in various forms, e.g., in liquid form, as a solution or suspension/dispersion, or in solid form. The amount of reaction product added to urea in accordance with this embodiment depends on the desired adduct content of the resulting fertilizer composition and on the adduct content of the reaction product, and can be readily calculated by those skilled in the art. It is noted that, in some embodiment, additional free NBPT can be added to the reaction product, the urea, or the combination thereof. Other components may be present in the adduct-containing fertilizer composition, which can be intentionally added or which can be inherently present in one or more of the composition components. For example, the compositions can comprise, in addition to the urea and reaction product components, some moisture, urea synthesis byproducts, solvent(s), and as noted further herein, may optionally contain other additives, such as dye(s), NBPT stabilizer(s), and/or micronutrient(s).

Other Optional Components (Applicable to all Compositions Disclosed Herein)

Other optional components may be used in compositions of the present invention. Examples of other such components include but are not limited to: nitrification inhibitors; conditioners; xanthan gum; calcium carbonate (agricultural lime) in its various forms for adding weight and/or raising the pH of acidic soils; metal containing compounds and minerals such as gypsum, metal silicates, and chelates of various micronutrient metals such as iron, zinc and manganese; talc; elemental sulfur; activated carbon, which may act as a "safener" to protect against potentially harmful chemicals in the soil; plant protectants; nutrients; nutrient stabilizers; super absorbent polymers; wicking agents; wetting agents; plant stimulants to accelerate growth; inorganic nitrogen, phosphorus, potassium (N—P—K) type fertilizers; sources of phosphorus; sources of potassium; organic fertilizers; surfactants, such as alkylaryl polyether alcohols; initiators; stabilizers; cross linkers; antioxidants; UV stabilizers; reducing agents; dyes, such as blue dye (FD & C blue #1); pesticides; herbicides; fungicides; and plasticizers. The content of the additional component(s) disclosed herein can be from about 1 to about 75 percent by weight of the composition and depends, in part, on the desired function of the additional component(s) and the makeup of the composition to which the additional component(s) are added.

Examples of conditioners include but are not limited to tricalcium phosphate, sodium bicarbonate, sodium ferricyanide, potassium ferricyanide, bone phosphate, sodium silicate, silicon dioxide, calcium silicate, talcum powder, bentonite, calcium aluminum silicate, stearic acid, and polyacrylate powder. Examples of plant protectants and nutrient stabilizers include silicon dioxide and the like. Examples of nutrients include, but are not limited to, phosphorus and potassium based nutrients. A commercially available fertilizer nutrient can include, for example, K-Fol 0-40-53, which is a solution that contains 40 wt. % phosphate and 53 wt. % potassium, which is manufactured and distributed by GBS Biosciences, LLC.

Nitrification inhibitors are compounds which inhibit the conversion of ammonium to nitrate and reduce nitrogen losses in the soil. Examples of nitrification inhibitors include, but are not limited to, dicyandiamide (DCD), and the like. Although the compositions disclosed herein can include DCD, in certain embodiments, the compositions are substantially free of DCD. "Substantially free" means that either no DCD can be detected in the mixture or, if DCD can be detected, it is (1) present in <1% w/w (preferably, <0.85% w/w, <0.80% w/w, or <0.75% w/w); and (2) does not produce effects characteristic of DCD at higher proportions. For example, a composition substantially free of DCD would not produce the environmental effects of exposure to concentrated or pure DCD even if a trace amount of DCD could be detected in the mixture. Certain exemplary compositions can have a DCD content of less than about 0.85% by weight, less than about 0.80% by weight, less than about 0.75% by weight, less than about 0.5% by weight, or less than about 0.25% by weight.

EXAMPLES

In order to provide a better understanding of the foregoing discussion, the following non-limiting examples are offered. Although the examples may be directed to specific embodiments, they are not to be viewed as limiting the invention in any specific respect. All parts, proportions, and percentages are by weight unless otherwise indicated.

Example 1: Synthetic Preparation of Adducts

As a representative example, to a solution of NBPT (5.0 g, 29.90 mmol) in N-methylpyrrolidone (NMP, 25 mL), was added to ACS-grade urea (1.79 g, 29.90 mmol, 1 equiv), followed by formalin (50%, 795 μL, 29.90 mmol, 1 equiv) at room temperature. The reaction mixture was stirred for 24 h. A homogeneous solution was obtained, containing ~10% unreacted NBPT (as evaluated by HPLC) and adducts, among other species.

TABLE 1

Adduct Formation Observed With Different Reactants and Reaction Conditions

| Run # | Reactants | Concentration of NBPT (wt. %) | Solvent | Temp (° C.) | Reaction Time (hrs) | NBPT conversion (%, HPLC) |
|---|---|---|---|---|---|---|
| 1 | NBPT + HCHO 37% + ACS-U$^a$ (1:1:1) | 15 | water | 25° C. | 24 | 82 |
| 2 | NBPT + dimethylolurea (1:1) | 13 | water | 25° C. | 24 | 98.9 |
| 3 | NBPT + dimethylolurea (1:1) | 13 | water | 25° C. | 144 | 99.9 |
| 4 | NBPT + dimethylolurea (1:1) | 13 | water | 40° C. | 24 | 96 |
| 5 | NBPT + dimethylolurea (1:4) | 9 | water | 40° C. | 24 | 99.2 |
| 6 | NBPT + reg-U$^b$ | 0.027 | water | 25° C. | 24 | <1 |
| 7 | NBPT + reg-U$^b$ | 0.027 | water (MAP added as catalyst) | 25° C. | 24 | 26 |
| 8 | NBPT + HCHO 50% + ACS-U$^a$ (1:0.5:1) | 15 | NMP | 25° C. | 24 | 67 |
| 9 | NBPT + HCHO 50% + ACS-U$^a$ (1:0.5:1) | 15 | propylene glycol | 25° C. | 24 | 40 |
| 10 | NBPT + HCHO 50% + ACS-U$^a$ (1:0.5:1) | 15 | propylene carbonate | 25° C. | 24 | 55 |
| 11 | NBPT + HCHO 50% + ACS-U$^a$ (1:0.5:1) | 15 | acetonitrile | 25° C. | 24 | 33 |
| 12 | NBPT + HCHO 50% + AC.S-U$^a$ (1:1:2) | 14 | NMP | 25° C. | 24 | 98.7 |
| 13 | NBPT + HCHO 50% + AC.S-U$^a$ (1:2:2) | 13 | NMP | 25° C. | 24 | 98.7 |
| 14 | NBPT + HCHO 50% + AC.S-U$^a$ (1:1:1) | 15 | NMP | 25° C. | 24 | 90 |
| 15 | NBPT + HCHO 50% + AC.S-U$^a$ (1:1:1) | 40 | NMP | 25° C. | 24 | 91 |
| 16 | NBPT + HCHO 50% + ACS-U$^a$ (1:1:1) | 55 | NMP | 25° C. | 24 | 92 |
| 17 | NBPT + HCHO 50% + ACS-U$^a$ (1:1:1) | 15 | NMP | 40° C. | 24 | 79 |

TABLE 1-continued

Adduct Formation Observed With Different Reactants and Reaction Conditions

| Run # | Reactants | Concentration of NBPT (wt. %) | Solvent | Temp (° C.) | Reaction Time (hrs) | NBPT conversion (%, HPLC) |
|---|---|---|---|---|---|---|
| 18 | NBPT + urea formaldehyde concentrate (1:1) | 50 | none | 25° C. | 24 | 80 |
| 19 | NBPT + urea formaldehyde concentrate (1:1) | 33 | NMP | 25° C. | 24 | 95 |
| 20 | NBPT + urea formaldehyde concentrate (1:1) | 25 | NMP (MAP added as catalyst) | 25° C. | 24 | 99 |
| 21 | NBPT + urea formaldehyde concentrate (1:1) | 25 | NMP/potassium phosphate buffer pH 7 | 25° C. | 24 | 99.9 |
| 22 | NBPT + urea formaldehyde concentrate (1:4) | 13 | NMP | 25° C. | 24 | 99.7 |
| 23 | NBPT + urea formaldehyde concentrate (1:1) | 33 | NMP | 40° C. | 24 | ~100 |

[a]ACS-U is ACS-grade urea, which is determined as being formaldehyde and/or UF free.
[b]Reg-U is commercial grade urea that contains approx. 0.4 wt. % formaldehyde as UF.

Example 2: Catalyst Effect

Urea (>99% pure) was treated at 260 ppm with a solution of AGROTAIN® PRIME (i.e., NBPT-containing solution); note that the formaldehyde is already present in the urea. After one day, the resulting AGROTAIN® treated urea (ATU) was blended with monoammonium phosphate (MAP) 50:50 wt. %, diammonium phosphate (DAP) 50:50 wt. % or ammonium sulfate (AMS) 50:50 wt. %. The blends were retained for 6 months and samples were retrieved for analysis at defined time points. ATU was separated from the other blend components prior to analysis by HPLC for NBPT content and by LC-MS to characterize NBPT and adducts.

TABLE 2

Adduct Formation in the Presence of MAP

| Day | Free NBPT (HPLC) | LC-MS Peak Area | | | |
|---|---|---|---|---|---|
| | | Free NBPT | Adduct 1 | Adduct 2 | Adduct 3 |
| 0 | 270 | 1421.5 | 0 | 0 | 0 |
| 1 | 170 | 947.9 | 78.8 | 0 | 0 |
| 2 | 120 | 637.9 | 202.4 | 6.4 | 28.1 |
| 3 | 90 | 516.7 | 253.1 | 8.5 | 45.0 |
| 4 | 70 | 311.8 | 210.7 | 8.7 | 51.8 |
| 7 | 50 | 219.3 | 238.2 | 11.9 | 74.3 |
| 8 | 40 | 196.0 | 230.9 | 9.6 | 72.2 |
| 9 | 30 | 207.9 | 200.7 | 10.5 | 73.4 |
| 10 | 30 | 94.3 | 145.7 | 8.4 | 50.5 |
| 11 | 30 | 129.9 | 179.3 | 8.1 | 71.7 |
| 14 | 20 | 75.2 | 128.2 | 7.8 | 48.0 |
| 16 | 10 | 91.5 | 138.2 | 8.2 | 58.1 |
| 18 | 10 | 76.9 | 126.3 | 8.7 | 57.7 |
| 21 | 10 | 51.6 | 87.3 | 3.6 | 39.7 |
| 24 | 10 | 48.1 | 93.4 | 5.1 | 43.3 |
| 28 | 8 | 38.5 | 84.2 | 4.5 | 36.0 |
| 31 | 6 | 29.7 | 81.1 | 2.7 | 41.3 |

TABLE 3

Adduct Formation in the Presence of DAP

| Day | Free NBPT (HPLC) | LC-MS Peak Area | | | |
|---|---|---|---|---|---|
| | | Free NBPT | Adduct 1 | Adduct 2 | Adduct 3 |
| 0 | 270 | 1421.5 | 0 | 0 | 0 |
| 2 | 200 | 882.2 | 80.6 | 0 | 5.5 |
| 3 | 170 | 795.5 | 110.8 | 2.7 | 8.7 |
| 4 | 150 | 812.5 | 189.0 | 4.8 | 18.5 |
| 7 | 140 | 624.0 | 240.5 | 6.5 | 26.0 |
| 8 | 130 | 712.8 | 245.9 | 5.8 | 23.7 |
| 9 | 110 | 454.1 | 238.1 | 6.5 | 27.7 |
| 10 | 100 | 448.0 | 272.9 | 7.0 | 39.2 |
| 11 | 80 | 563.6 | 349.0 | 9.0 | 49.5 |
| 14 | 70 | 339.6 | 322.2 | 8.8 | 58.0 |
| 16 | 60 | 239.1 | 304.4 | 10.9 | 63.7 |
| 18 | 60 | 299.0 | 365.8 | 10.9 | 68.4 |
| 21 | 50 | 196.4 | 377.1 | 9.8 | 87.5 |
| 24 | 50 | 175.1 | 373.9 | 14.3 | 101.8 |
| 28 | 40 | 197.4 | 395.2 | 15.8 | 103.3 |
| 31 | 30 | 148.9 | 355.3 | 16.6 | 108.0 |

TABLE 4

Adduct formation in the Presence of AMS

| Day | Free NBPT (HPLC) | LC-MS Peak Area | | | |
|---|---|---|---|---|---|
| | | Free NBPT | Adduct 1 | Adduct 2 | Adduct 3 |
| 0 | 270 | 1421.5 | 0 | 0 | 0 |
| 2 | 200 | 850.1 | 74.0 | 4.4 | 7.8 |
| 3 | 190 | 1022.9 | 124.6 | 2.7 | 8.5 |
| 4 | 190 | 873.5 | 145.1 | 5.3 | 13.7 |
| 7 | 170 | 708.9 | 243.6 | 6.3 | 30.5 |
| 8 | 170 | 740.5 | 232.3 | 5.6 | 29.2 |
| 9 | 150 | 661.9 | 245.7 | 7.3 | 34.6 |
| 10 | 140 | 871.5 | 320.7 | 7.8 | 45.3 |
| 11 | 140 | 613.9 | 233.9 | 4.9 | 32.3 |
| 14 | 120 | 602.8 | 288.3 | 6.5 | 39.9 |
| 16 | 120 | 556.3 | 336.3 | 9.2 | 54.1 |

TABLE 4-continued

Adduct formation in the Presence of AMS

| Day | Free NBPT (HPLC) | LC-MS Peak Area | | | |
|---|---|---|---|---|---|
| | | Free NBPT | Adduct 1 | Adduct 2 | Adduct 3 |
| 18 | 100 | 632 | 372.8 | 10.2 | 59.9 |
| 21 | 110 | 497.2 | 367.0 | 7.8 | 54.4 |
| 24 | 120 | 420.1 | 319.2 | 8.3 | 50.8 |
| 28 | 140 | 535.8 | 214.8 | 7.3 | 44.5 |
| 31 | 80 | 479.1 | 415.0 | 13.9 | 80.3 |

Example 3: Determination of Urease Inhibition

The effectiveness of urease inhibition was measured as follows. One tbsp of water was used to moisten 4 oz (~100 g) of Tifton, Ga. soil of pH 7.7. The moist soil was placed in an 8 oz plastic cup with a tight-fitting lid. Approximately 1 tsp (~2 g) of NBPT- and/or adduct-treated urea granules, was applied to the soil surface and the container was sealed. The container was incubated at room temperature for three days and analyzed for ammonia volatilization by inserting an ammonia-sensitive Drager tube through the lid of the sealed container. In this way, the amount of ammonia present in the headspace of the container was quantified up to 600 ppm, the limit of the Drager tube. In general, more effective urease inhibitors are characterized by having lower concentrations of ammonia in the headspace. All tests were run in duplicate in the presence of a positive control (i.e., untreated urea), which typically exhibits >600 ppm ammonia after 3 days following application.

Various compositions comprising NBPT and/or the adducts disclosed herein were prepared by combining NBPT and/or adducts with urea granules; and urease inhibition was determined using the methodology described above. The adducts used in this example were prepared according to entry 14, in Table 1, above.

The data in FIG. 1 show the effect of various urease inhibitors, namely NBPT and/or the adducts disclosed herein, on volatilization of ammonia from treated urea exposed to soil according to the method outlined above. For comparison purposes, the data is presented according to the phosphorous content (i.e. ppmP as measured by ICP), of the various inhibitors used to treat the urea. These data show that increasing the amount of NBPT with respect to the urea content in the range of 111-196 ppmP has no significant effect on the onset of significant ammonia volatilization. For example, the onset of significant ammonia volatilization (arbitrarily chosen as ≥100 ppm) is comparable for urea treated with varying amounts of NBPT at about Day 8 following application, i.e., ATU 111 ppmP=ATU 128 ppmP=ATU 196 ppmP. However, when some of the NBPT is replaced with the adducts disclosed herein—at the same phosphorus content—a noticeable delay in the onset of significant ammonia volatilization is observed e.g., ≥100 ppm ammonia at no earlier than Day 9 following application, i.e., 'NBPT/Adducts $^{42}/_{69}$ ppmP'>ATU 111 ppmP. Further, when NBPT and the adducts disclosed herein are combined with urea in a ratio of NBPT:adducts of 1:1 by phosphorus content, the onset of significant ammonia volatilization is not observed until after Day 10 following application, i.e., 'NBPT/Adducts 111/85 ppmP'>>ATU 196 ppmP. Surprisingly, adducts alone do not outperform an equivalent amount of NBPT, i.e., 'Adducts 111 ppmP'=ATU 111 ppmP. This confirms the synergistic relationship between NBPT and the adducts disclosed herein, as described above.

Example 4: Volatilization Analysis

Cumulative N loss through volatilization was determined over a span of 14 days for NBPT- and/or adduct-treated urea granules applied to soil at a pH of 5.05. In general, more effective urease inhibitors are characterized by having lower production of N. All tests were run in duplicate in the presence of a control (i.e., unfertilized soil).

Soil (pH of 5.05) was obtained (representing the surface 4 inches of soil from a given location) and the soil was air dried, passed through a 2-mm sieve, and homogeneously mixed with a cement mixer. Portions of the air dried soil (500 g each) were transferred to individual jars. The soil moisture in each jar was adjusted to ⅔ of water holding capacity by adding deionized water and thoroughly mixing to ensure consistent moisture throughout the soil within each jar. Once the moisture was equilibrated throughout the soil, the jars were placed inside a temperature controlled wooden cabinet for 24 h to equilibrate the moistened soil to 26° C. Three N sources were evaluated, including two experimental urease inhibitor-treated ureas and untreated urea. In addition, an untreated soil was included to evaluate background ammonia levels. The urea for all treatments was passed through an 8-mesh sieve and retained on a 10 mesh sieve to ensure uniformity. Nitrogen sources were applied at an equivalent rate of 120 pounds of N per acre based on the surface area of the soil in the jar. Each treatment was replicated 4 times and randomly placed into four separate chambers containing four jars each.

Air flow rates through the soil chambers were controlled at 1.00 L min$^{-1}$ and temperature was maintained at 26° C. Acid traps containing 100 mL of 0.02 M ortho-phosphoric acid were used to capture volatilized NH$_3$ in the air stream flowing over the soil surface. Acid traps were changed at 24, 48, 72, 96, 120, 144, 168, 216, 264, 312, and 336 h (2 wk) after initiation of the trial. Acid traps were weighed and the total volume of solution was calculated using the density of 0.02 M phosphoric acid at 25° C. Ammonical N concentration in the acid traps was determined colorimetrically using a Lachat QuickChem Automated Ion Analyzer (Lachat Instruments, Loveland, Colo.). The trial was analyzed as a randomized block design with four replications (blocks). Each trial was analyzed separately using analysis of variance (ANOVA) using Proc Mixed in SAS (SAS Institute, 2009). Least significant difference (LSD) mean separation was used to determine treatment differences in cumulative N captured in acid traps at α=0.05. Maximum loss rates were calculated by dividing the percent NH$_3$ lost during a sampling interval by the duration (hours) of the sampling intervals.

Table 2, below, provides the results of the study, wherein soil N source K1 represents urea treated only with carriers (N-methyl pyrrolidone and a dye), soil N source K2 represents ATU (111 ppmP), and soil N source K3 represents adduct-treated urea (adduct/NBPT, 55 ppmP/55 ppmP). The adduct-treated urea used in this example was prepared according to entry 14, in Table 1, above.

TABLE 4

Cumulative N Loss Through Volatilization

| Soil N Source | Cumulative N Loss (mg/kg) | | | | | | | | | | | |
|---|---|---|---|---|---|---|---|---|---|---|---|---|
| | Day 0 | Day 1 | Day 2 | Day 3 | Day 4 | Day 5 | Day 6 | Day 7 | Day 9 | Day 10 | Day 12 | Day 14 |
| K1 | 0.00 | 1.89$^a$ | 21.65$^a$ | 26.18$^a$ | 28.26$^a$ | 29.50$^a$ | 30.34$^a$ | 31.39$^a$ | 31.72$^a$ | 32.13$^a$ | 32.32$^a$ | 32.38$^a$ |
| K2 | 0.00 | 0.02$^b$ | 1.77$^b$ | 5.08$^b$ | 8.02$^b$ | 10.45$^b$ | 12.25$^b$ | 14.13$^b$ | 14.65$^b$ | 15.27$^b$ | 15.56$^b$ | 15.65$^b$ |
| K3 | 0.00 | 0.02$^b$ | 0.46$^b$ | 1.50$^b$ | 3.01' | 4.79$^b$ | 6.73$^b$ | 9.51$^b$ | 10.21$^b$ | 10.99$^b$ | 11.36$^b$ | 11.47$^b$ |
| Unfertilized Soil | 0.00 | 0.00 | 0.00 | 0.00 | 0.00 | 0.00 | 0.00 | 0.00 | 0.00 | 0.00 | 0.00 | 0.00 |
| LSD P = 0.05 | | 1.000 | 3.690 | 3.986 | 4.824 | 5.678 | 6.461 | 7.606 | 7.871 | 8.162 | 8.289 | 8.326 |
| Standard deviation | 0.000 | 0.550 | 2.030 | 2.193 | 2.654 | 3.124 | 3.554 | 4.184 | 4.330 | 4.490 | 4.560 | 4.580 |
| CV | 0.00 | 85.66 | 25.51 | 20.08 | 20.26 | 20.95 | 21.62 | 22.81 | 22.96 | 23.07 | 23.09 | 23.10 |
| Replicate F | 0.000 | 0.828 | 1.401 | 1.789 | 1.396 | 0.923 | 0.596 | 0.352 | 0.318 | 0.292 | 0.281 | 0.278 |
| Replicate Prob(F) | 1.000 | 0.533 | 0.345 | 0.266 | 0.346 | 0.494 | 0.644 | 0.790 | 0.813 | 0.830 | 0.837 | 0.840 |
| Treatment F | 0.00 | 15.39 | 136.80 | 148.02 | 101.49 | 68.74 | 48.31 | 30.40 | 27.52 | 24.77 | 23.65 | 23.35 |
| Treatment Prob(F) | 1.000 | 0.007 | 0.000 | 0.000 | 0.000 | 0.000 | 0.001 | 0.002 | 0.002 | 0.003 | 0.003 | 0.003 |

Figure 2:
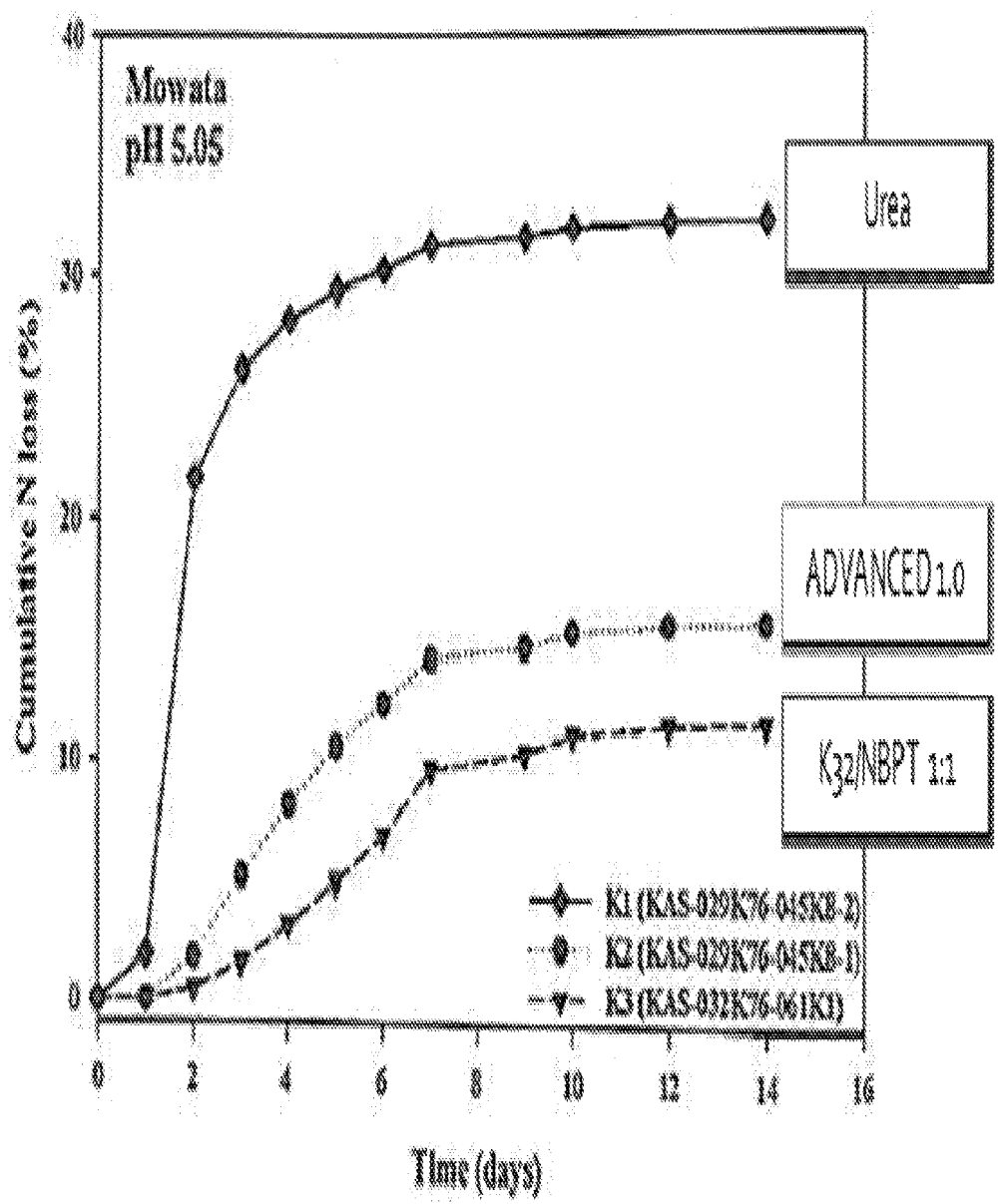
FIG. 2 is a plot of cumulative N loss (measured in %) from urea and urease inhibitor-treated ureas.

$^a$Means followed by same letter or symbol do not significantly differ (P = 0.05, LSD)
$^b$Means comparison performed only when AOV Treatment (P(F) is significant at mean comparison OSL
$^c$Untreated treatment 4 excluded from analysis The data presented in Table 5 clearly shows that the adduct-treated urea (K3) gave significantly less N loss through volatilization than either the urea treated only with carriers (K1) and the ATU (K2) beginning on Day 2 following application to the acidic soil in this study. After 2 days, the adduct-treated urea (K3) gave a 98% reduction in N loss as compared with urea treated only with carriers (K1) and performed 75% better than the ATU (K2). After 14 days, the adduct-treated urea (K3) gave a 65% reduction in N loss as compared with the urea treated only with carriers (K1) and performed 25% better than the ATU (K2). Furthermore, maximum N loss by volatilization was delayed by 2-3 days using the adduct treated urea (K3) as compared with that exhibited by ATU (K2), even in acidic soil (compare K3 day 7 with the equivalent loss of N for K2 on the curve generated from this data in FIG. 2, day 4-5).

The invention claimed is:

1. A fertilizer composition comprising urea and one or more adducts,
   wherein the adducts are selected from the following structures:

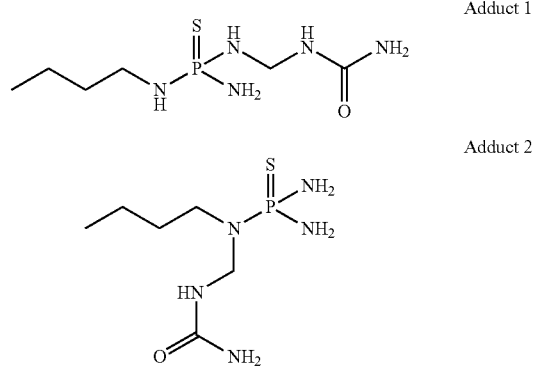

Adduct 1

Adduct 2

Adduct 3 and wherein the urea is present in an amount of at about 90% by weight or more, based on total weight of the fertilizer composition.

2. The fertilizer composition of claim 1, wherein the urea is present in an amount of at about 98% by weight or more, based on total weight of the fertilizer composition.

3. The fertilizer composition of claim 1, wherein the one or more adducts are present in an amount of 20 ppmP to 1000 ppmP, based on total weight of the fertilizer composition.

4. The fertilizer composition of claim 1, further comprising N-(n-butyl)thiophosphoric triamide (NBPT).

5. The fertilizer composition of claim 4, further comprising formaldehyde.

6. The fertilizer composition of claim 4, wherein the one or more adducts and the NBPT are present in a weight ratio, as measured by phosphorus content, of 4:1 to 1:4.

7. The fertilizer composition of claim 4, wherein the one or more adducts and the NBPT are present in a weight ratio, as measured by phosphorus content, of 2:1 to 1:2.

8. The fertilizer composition of claim 4, wherein the one or more adducts and the NBPT are present in a weight ratio, as measured by phosphorus content, of about 1:1.

9. A composition comprising NBPT and one or more adducts,
   wherein the adducts are reaction products formed from urea, formaldehyde, and NBPT; and wherein the adducts comprise from the following structures:

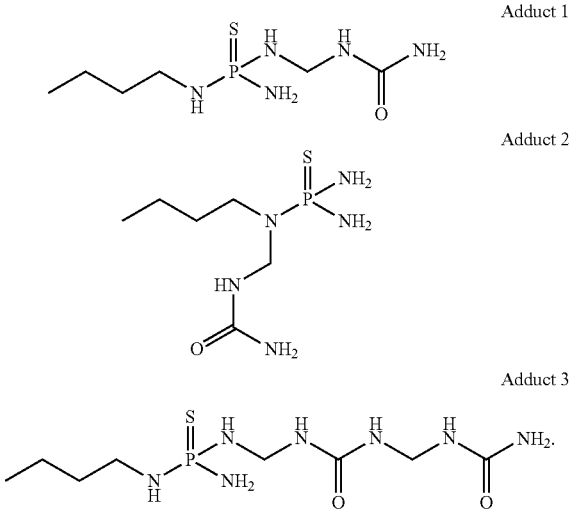

10. The composition of claim 9, wherein the one or more adducts and the NBPT are present in a weight ratio, as measured by phosphorus content, of 4:1 to 1:4.

11. The composition of claim 9, wherein the one or more adducts and the NBPT are present in a weight ratio, as measured by phosphorus content, of 2:1 to 1:2.

12. The composition of claim 9, wherein the one or more adducts and the NBPT are present in a weight ratio, as measured by phosphorus content, of about 1:1.

13. The composition of claim 9, wherein the NBPT and one or more adducts are in solution comprising at least one solvent selected from the group consisting of NMP, glycol, glycol derivatives, protected glycols, acetonitrile, DMSO, alkanolamines, alkylsulfones, monoalcohols, dibasic esters and derivatives thereof, alkylene carbonates, monobasic esters, carboxylic acids, and glycol esters.

14. A fertilizer composition of claim 9, further comprising urea.

15. A fertilizer composition comprising a mixture of NBPT and one or more adducts,
  wherein the adducts are reaction products formed from a urea source, a formaldehyde source, and NBPT;
  wherein the mixture is present in an amount from 50 ppmP to 1000 ppmP, based on total weight of the fertilizer composition;
  wherein the urea source is not a urea-formaldehyde polymer (UFP).

16. The fertilizer composition of claim 15, wherein the one or more adducts and the NBPT are present in a weight ratio, as measured by phosphorus content, of 4:1 to 1:4.

17. The fertilizer composition of claim 15, wherein the one or more adducts and the NBPT are present in a weight ratio, as measured by phosphorus content, of 2:1 to 1:2.

18. The fertilizer composition of claim 15, wherein the one or more adducts and the NBPT are present in a weight ratio, as measured by phosphorus content, of about 1:1.

19. The fertilizer composition of claim 15, further comprising urea in an amount of at about 90% by weight or more, based on total weight of the fertilizer composition.

* * * * *